US011618618B2

(12) United States Patent
Greiner-Perth et al.

(10) Patent No.: US 11,618,618 B2
(45) Date of Patent: Apr. 4, 2023

(54) VENTED PROTECTIVE CAP FOR A LIQUID DISPENSER, VENTING INSERT, IN PARTICULAR FOR A PROTECTIVE CAP, LIQUID DISPENSER HAVING SUCH A PROTECTIVE CAP OR SUCH A VENTING INSERT, AND METHOD FOR PRODUCING A PROTECTIVE CAP OR A VENTING INSERT

(71) Applicant: Aptar Radolfzell GmbH, Radolfzell (DE)

(72) Inventors: Jürgen Greiner-Perth, Gottmadingen (DE); Andi Herz, Eigeltingen-Reute (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 319 days.

(21) Appl. No.: 16/857,964

(22) Filed: Apr. 24, 2020

(65) Prior Publication Data
US 2020/0339315 A1 Oct. 29, 2020

(30) Foreign Application Priority Data

Apr. 26, 2019 (EP) .................... 19171379

(51) Int. Cl.
*B65D 47/32* (2006.01)
*A61M 11/00* (2006.01)
*B65D 83/40* (2006.01)

(52) U.S. Cl.
CPC ........... *B65D 47/32* (2013.01); *A61M 11/006* (2014.02); *B65D 83/40* (2013.01);
(Continued)

(58) Field of Classification Search
CPC .... B65D 47/32; B65D 83/40; B65D 2205/00; B65D 51/1616; B65D 47/18;
(Continued)

(56) References Cited

U.S. PATENT DOCUMENTS 6,174,576 B1 1/2001 Van de Ponseele
8,794,490 B2 * 8/2014 Painchaud ............. B65D 51/18
222/521
(Continued)

FOREIGN PATENT DOCUMENTS

DE 1218305 B 6/1966
DE 102012214426 B3 8/2013
(Continued)

OTHER PUBLICATIONS

European Search Report issued in corresponding EP 19 17 1379 with English translation of categories of cited documents, dated Jan. 3, 2020 (8 pages).

*Primary Examiner* — Kareen K Thomas
(74) *Attorney, Agent, or Firm* — Flynn Thiel, P.C.

(57) ABSTRACT

A vented protective cap for a liquid dispenser, and a venting insert, in particular for such a protective cap. The protective cap has a cap wall which surrounds a cap interior. The cap wall has a venting aperture which is spanned by a flexible sheet-like structure. A boundary region of the sheet-like structure is fixed in an encircling manner to a boundary of the venting aperture. The sheet-like structure consists of at least two layers which bear directly against one another but, at least in a central region of the sheet-like structure, are not connected fixedly to one another.

18 Claims, 9 Drawing Sheets

(52) U.S. Cl.
CPC . *A61M 2205/0205* (2013.01); *A61M 2207/10* (2013.01); *B65D 2205/00* (2013.01)

(58) Field of Classification Search
CPC ............. B65D 51/1611; A61M 11/006; A61M 2205/0205; A61M 2207/10; A61F 9/0008; A61J 1/067; A61J 1/1412; A61J 1/145; B01D 46/0028; B01D 46/543; B29C 45/14; B29C 45/1418; B29C 2045/14237
See application file for complete search history.

(56) References Cited

U.S. PATENT DOCUMENTS

| | | | |
|---|---|---|---|
| 9,592,934 B2 * | 3/2017 | Painchaud | B05B 11/0032 |
| 10,202,224 B2 * | 2/2019 | Painchaud | B65D 50/041 |
| 2014/0048569 A1 | 2/2014 | Wochele et al. | |
| 2014/0332567 A1 * | 11/2014 | Geiger | B65D 47/18 |
| | | | 222/420 |
| 2014/0336596 A1 * | 11/2014 | Wochele | A61J 1/067 |
| | | | 604/298 |
| 2015/0166229 A1 * | 6/2015 | Wochele | B65D 41/48 |
| | | | 222/153.05 |
| 2016/0311588 A1 | 10/2016 | Wochele | |
| 2017/0362000 A1 | 12/2017 | Greiner-Perth et al. | |

FOREIGN PATENT DOCUMENTS

| | | |
|---|---|---|
| DE | 102013226253 B4 | 6/2015 |
| DE | 102016210992 B3 | 5/2017 |

\* cited by examiner

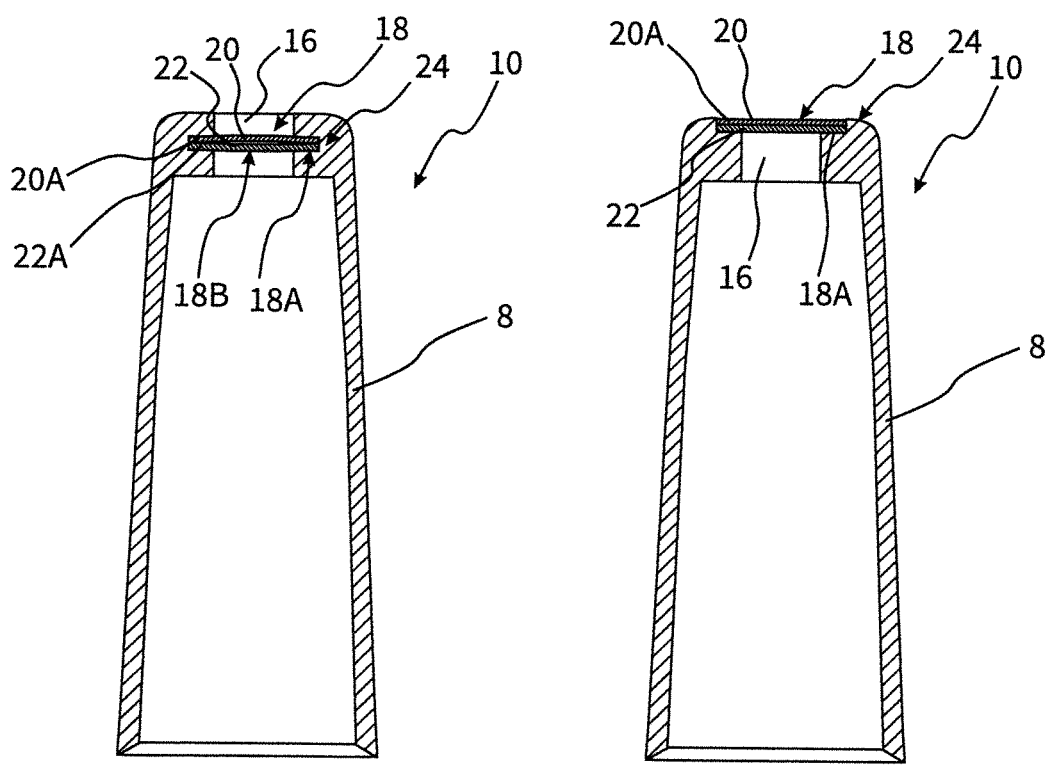
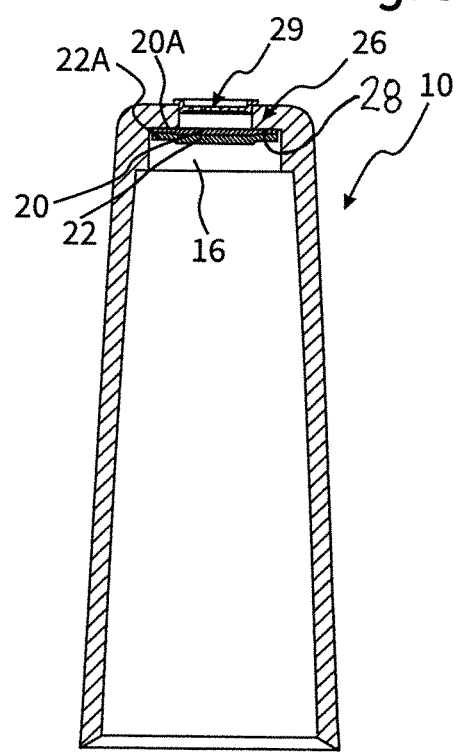

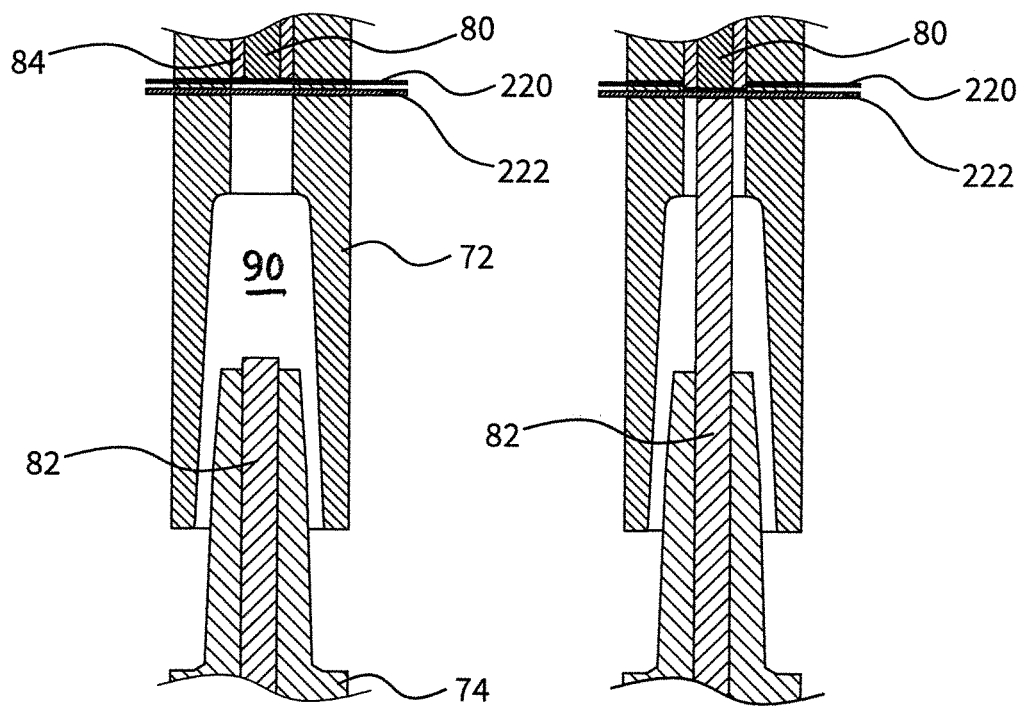
Fig. 7A
Fig. 7B
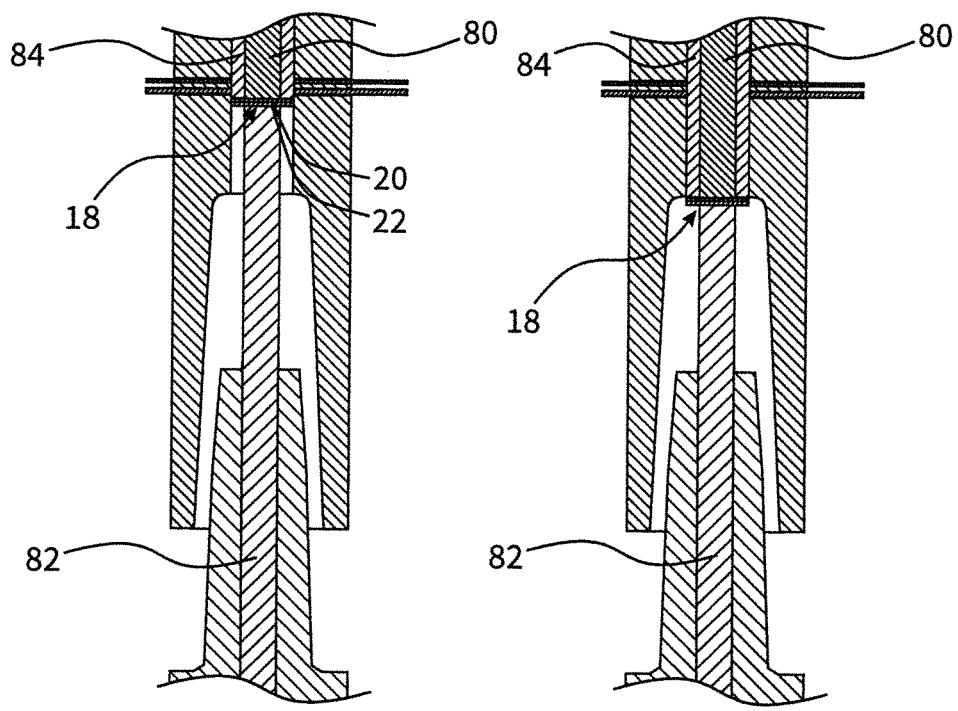
Fig. 7C
Fig. 7D

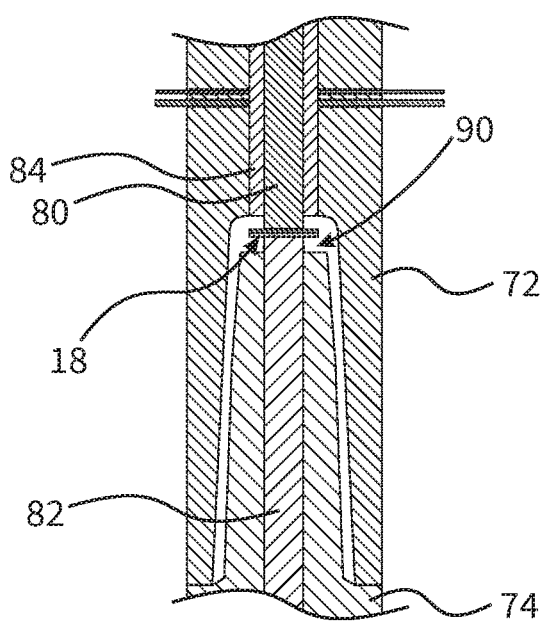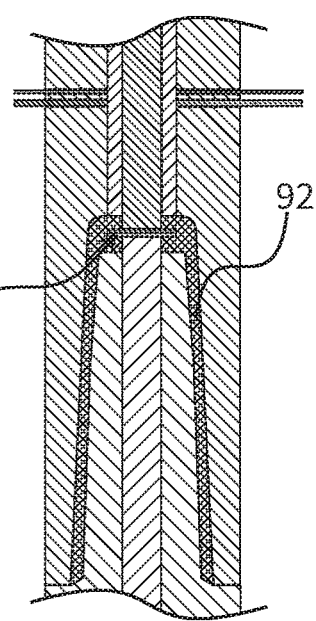
*Fig. 7E*     *Fig. 7F*
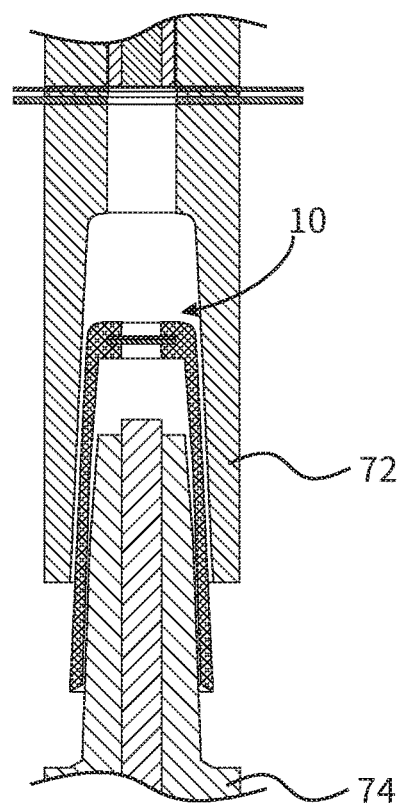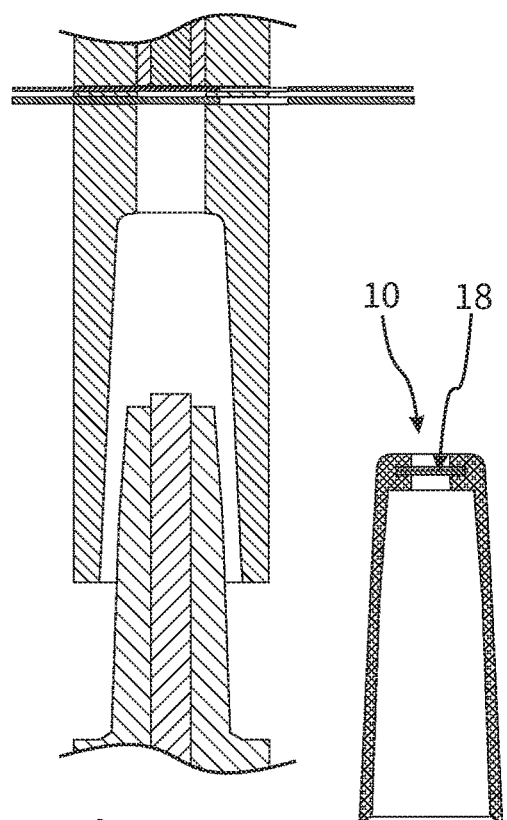
*Fig. 7G*     *Fig. 7H*

VENTED PROTECTIVE CAP FOR A LIQUID DISPENSER, VENTING INSERT, IN PARTICULAR FOR A PROTECTIVE CAP, LIQUID DISPENSER HAVING SUCH A PROTECTIVE CAP OR SUCH A VENTING INSERT, AND METHOD FOR PRODUCING A PROTECTIVE CAP OR A VENTING INSERT

CROSS-REFERENCE TO RELATED APPLICATIONS

This claims priority from European Application No. 19171379.1, filed Apr. 26, 2019, the disclosure of which is hereby incorporated by reference in its entirety into this application.

FIELD OF APPLICATION AND PRIOR ART

The invention relates to a vented protective cap, to a venting insert, in particular for such a protective cap, and to a liquid dispenser having such a protective cap. The invention furthermore also relates to corresponding production methods.

Vented protective caps are used in liquid dispensers for pharmaceutical liquids in order to permit after first use an exchange of air between a cap interior and surroundings. This serves the purpose of quicker drying of liquid residues which have remained beyond the discharge opening of a dispenser. In this way, growth of bacteria is prevented. However, the venting openings of vented protective caps for their part also lead to the risk of germs being introduced from the surroundings, so that provision of the venting opening with a sterile filter has already been proposed.

It is known from DE 102013226253 B4 for provision to be made of such a sterile filter on the cap. Here, the stated document also already proposes the use of a two-layer insert which consists of a thin carrier covering on which the sterile filter is fixedly attached.

The use of such a multi-layer structure is advantageous in order to be able to perform multiple functions. However, the production of a multi-layer flexible sheet-like material is relatively cumbersome, such that such a material is worthwhile only for large-series production or with significantly increased production costs.

Problem and Solution

It is an object of the invention to provide a vented protective cap or a venting insert, in particular for such a protective cap, which permits adaptation to specific requirements in an inexpensive manner.

For the purpose of achieving said object, a vented protective cap for a liquid dispenser that has a cap wall which surrounds a cap interior is proposed. The cap wall has a venting aperture which is spanned by a flexible sheet-like structure. A boundary region of the sheet-like structure is fixed in an encircling manner to a boundary of the venting aperture.

The sheet-like structure of a protective cap according to the invention consists of at least two layers which bear directly against one another but, at least in a central region of the sheet-like structure, are not connected fixedly to one another.

The sheet-like structure spans the at least one venting aperture and thus ensures that, with the protective cap mounted, an exchange of air between a cap interior and the surroundings is possible only through the sheet-like structure. The sheet-like structure has a plurality of layers, which preferably perform different functions. Said layers are handled separately during production and, at least in a central region of preferably at least 9 mm$^2$, are not directly connected to one another. During the course of production, however, said layers can be connected to one another in a boundary region, in particular by common encapsulation with plastic or by thermal joining.

As a result of the at least two layers, which do not together originate from a composite material, but rather are each produced individually from sheets or bands of their specific type, a high degree of flexibility is provided. The multiple layers may also be put together for small series of dispensers in a requirement-specific manner.

By way of example, mention may be made of the following layers, which may be part of a sheet-like structure of the dispenser cap according to the invention.

A layer which is formed as a sterile filter is normally included. This preferably has a separation limit of at most 1 µm in size, in particular preferably a separation limit of at most 0.5 µm in size. Even better sterility can be achieved with a separation limit of at most 0.2 µm in size. Such a sterile filter prevents the entry of germs through the venting aperture.

The filter layer may be formed as a deep-bed filter or as a membrane filter. The deep-bed filter has a three-dimensional structure into which bacteria can enter but which separates the bacteria from the air flowing through. In the membrane filter, provision is made of pores of a defined size, by means of which germs are already separated out before entering the layer.

A layer of the sheet-like structure may be formed as an absorbent layer, which is provided for absorbing a residual drop from a discharge opening of the dispenser, wherein, proceeding from the cap interior, said layer preferably constitutes the first layer of the sheet-like structure. Said absorbent layer, with the protective cap mounted, may bear directly against the end surface of the main unit of the dispenser or be slightly spaced apart from said end surface.

The layers may have a hydrophilic surface or a hydrophobic surface. In this respect, it may be expedient for example to configure an absorbent layer to be hydrophilic in order to accelerate the absorption of liquid. It is also possible for multiple layers to be configured to be hydrophilic to different degrees in order, in this way, for residual liquid to be absorbed and to be guided to a particularly hydrophilic core layer.

It may also be expedient for provision to be made of a layer which is formed to be antibacterial or comprises a bactericidal constituent. In this way, bacteria contained in the air or in absorbed liquid can be killed when passing through the layers and at least the growth thereof can be reduced.

It is also possible for a layer of the sheet-like structure to be formed as a support layer, in particular an outermost layer. Such a support layer can impart mechanical stability to the sheet-like structure. This allows further layers of the sheet-like structure to be protected against inadvertent or deliberate damage.

A type of stiff fabric may be involved here. A design having multiple support layers, in particular on both sides of a sterile filter layer, may also be expedient.

A further layer which is expedient is a screening layer, which screens from view at least one layer situated below it. This is expedient in particular for protective caps which have a coloured design. Since sterile filters normally have a technically determined colouring and are often white, these stand out immediately on coloured protective caps and possibly give rise to the misunderstanding that the corresponding layer should be removed according to intended use. A screening layer having the colouring of the plastic of the protective cap conceals the sterile filter and therefore prevents any misunderstanding.

In a first variant of a protective cap according to the invention, it is provided that the at least two layers of the sheet-like structure are held at the boundary of the venting aperture by a common injection-moulded bearing structure. It is provided here that the bearing structure, on one side or in particular preferably integrally on both sides of the sheet-like structure, projects over the boundary region of the sheet-like structure.

In particular, the holding on both sides is considered to be advantageous. In this case, two encircling webs of the bearing structure above and below the flexible sheet-like structure project over the latter and in this way fix the sheet-like structure. The production is preferably realized in that the multi-layer sheet-like structure is firstly introduced into an injection moulding cavity, and is then encapsulated by plastic which in the process forms the stated two encircling webs.

Other designs having only one such web may also be expedient, however. The layers facing away from said web are then held circumferentially by plastic material. In particular in the case of porous layers such as a deep-bed filter, a firm connection to the plastic of the cap can be provided despite the only small surface on the circumference.

In another variant of a protective cap according to the invention, it is provided that a bearing structure having a ring-shaped fastening surface is provided at the boundary of the venting aperture. A first layer of the sheet-like structure is, in a boundary region, thermally fastened to said fastening surface. A second layer of the sheet-like structure is, in a boundary region, thermally fastened at least also to the boundary region of the first layer.

In this type of design, the layers of the sheet-like structure are not encapsulated, but rather are thermally fastened to the stated fastening surface or to one another. The connection is preferably produced in this case by means of a hollow embossing stamp, which compresses and melts away the respective layers in the boundary region such that said layers form an intimate connection to one another or to the fastening surface. Other joining techniques such as laser welding and ultrasonic welding are also possible here.

The protective cap may have a main component which at least predominantly forms a lateral wall of the cap wall and on which the bearing structure is provided integrally. In such a case, with the exception of the layers of the sheet-like structure over the venting aperture, the cap can thus be produced integrally.

Besides this design with the bearing structure provided integrally on the lateral wall, it may also be provided that the protective cap has a main component which at least predominantly forms a lateral wall of the cap wall and which has an opening for receiving a venting insert. In this case, the protective cap has as a further component a venting insert which is inserted sealingly into the opening and which comprises the surrounding bearing structure and the sheet-like structure held and surrounded by the latter.

Although such a modular construction is associated with a slightly higher outlay in terms of production, it permits the use of unitary main components and the requirement-specific adaptation thereof through the use of a suitable venting insert.

In a simple construction of a protective cap according to the invention, it is provided that provision is made of only one venting aperture, which is not segmented by way of the bearing structure or sections integrally connected thereto. It may be advantageous in particular in those cases where the protective cap has a protective structure for protecting the sheet-like structure, wherein the protective structure is formed as a component which is separate from the bearing structure and is connected in a force-fitting manner or form-fitting manner to the bearing structure. Said protective structure, which is preferably produced as a separate plastic part, can protect the sheet-like structure to an even more reliable degree than the above-stated support layer.

Besides the cap, the invention also relates to the already described venting insert, in particular for use in a cap according to the invention.

Here too, it is provided that the venting insert has a venting aperture which is surrounded by a bearing structure, and that the venting aperture is spanned by a flexible sheet-like structure whose boundary region is fixed in an encircling manner to the bearing structure.

The sheet-like structure consists here of the already described at least two layers which bear directly against one another but, at least in a central region of the sheet-like structure, are not connected fixedly to one another. The layers which are possible here comprise all the layers stated above with regard to the protective cap.

As also for the protective cap described, it may also be provided for a corresponding venting insert that the two layers of the sheet-like structure are held at the boundary of the venting aperture by a common injection-moulded bearing structure, which, on one side or integrally on both sides of the sheet-like structure, projects over the boundary region of the sheet-like structure. Alternatively, it may also be provided here that a bearing structure having a ring-shaped fastening surface is provided at the boundary of the venting aperture, wherein a first layer of the sheet-like structure is, in a boundary region, thermally bonded to the fastening surface, and wherein a second layer of the sheet-like structure is, in a boundary region, thermally bonded to the boundary region of the first layer.

The connection of the venting insert may be fastened in a receptacle, in particular of the protective cap described, by means of different connection techniques. One preferred design provides that the venting insert has a tapering and preferably at least sectionally conical lateral surface which permits simple insertion and, if appropriate, the establishment of a self-locking press fit with respect to the receptacle.

Alternatives to this provide that the venting insert is fastened by means of a snap-action connection and accordingly has an outer geometry with snapping-behind capability. A threaded connection or an adhesive or welded connection is also possible. In the case of a welded connection, this may be produced in particular by means of laser welding or ultrasonic welding.

Besides the protective cap described and the venting insert described, the invention also relates to a liquid dispenser, in particular for pharmaceutical liquids. Said liquid dispenser has a main unit, which for its part comprises a liquid store and a conveying device and a discharge opening for releasing the liquid. The conveying device may be designed in particular as a pump device for conveying liquid stored free of pressure or as a valve device for conveying liquid stored pressurized in a pressure store. Liquid passes from the liquid store to the discharge opening upon manual actuation of the conveying device. Instead of a conveying device separated from the liquid store, the liquid store may also be provided with a squeeze bottle, that is to say a bottle which is able to be compressed by manual application of force and which thus itself constitutes the conveying device.

The liquid dispenser may in particular be designed as a drop dispenser, that is to say for releasing individual drops, in particular for application into the nose, into the ears or into the eyes. Such a drop dispenser preferably has, in a manner surrounding the discharge opening, a drop formation geometry, for example in the form of a concave or planar drop formation surface, which is preferably surrounded by a sharp-edged separating edge. It is advantageous, in particular for discharging preservative-free liquids, if a release valve is arranged upstream of the discharge opening and, here, prevents the introduction of germs, at the same time however also preventing a residual drop from being sucked back.

In particular for the purpose of quick drying of such a residual drop, according to the invention, the liquid dispenser has a vented protective cap of the above-described type which is able to be mounted onto the main unit and which protects the discharge opening in the mounted state. According to the invention, provision may be made of a venting insert of the above-described type on said protective cap or, in an alternative use, at another location of a liquid dispenser.

The use of a protective cap according to the invention and/or a venting unit according to the invention may be expedient with other dispensers too, for example with spray dispensers for atomized discharge of liquid too.

Here, the protective cap is preferably provided with a sheet-like structure having an absorbent or antibacterial layer, wherein said layer, with the protective cap mounted, is arranged directly above the discharge opening, with the result that a residual drop remaining at the discharge opening can be absorbed, and/or decontaminated, by this layer.

In the delivery state, the liquid dispenser is filled with a pharmaceutical liquid. This is in particular a pharmaceutical liquid for treatment of increased intraocular pressure (treatment of glaucoma), for treatment of dry eyes and for treatment of allergies and inflammations. In this case, in particular the molecular groups alpha-2-agonists, for example brimonidine, prostaglandin analogues (tafluprost, latanoprost, bimatoprost, travoprost), beta blockers, for example timolol, and carbonic anhydrase inhibitors, for example dorzolamide or hyaluronic acid compounds, film formers, for example methyl cellulose compounds, and ciclosporin or antihistamines, for example olopatadine and levocabastine, steroids, for example loteprednol and dexamethasone, and also NSAIDs, for example ketorolac, play a role.

The dispenser according to the invention is furthermore advantageously able to be used for liquids having molecules of one or of several of the following kinds: trichloroacetic acid, trioxysalen, urea, zinc oxide, tacrolimus, clobetasol propionate, mometasone furoate, betamethasone dipropionate, fluocinonide, desoximetasone, triamcinolone acetonide, fluticasone propionate, hydrocortisone, clotrimazole, ketoconazole, miconazole, undecylenic acid, terbinafine, ciclopirox, tolnaftate, acyclovir, imiquimod, docosanol, finasteride, minoxidil, dexamethasone, tramazoline, naphazoline, nostrilla, oxymetazoline, phenylephrine, phenylpropanolamine, pseudoephedrine, tetryzoline, tramazoline hydrochloride, tuaminoheptane and xylometazoline.

The invention furthermore also relates to a method for producing a protective cap of the above-described type or a venting insert of the above-described type. This will be explained below primarily on the basis of a protective cap, wherein the method steps can also correspondingly be used for producing a separate venting insert, which is then subsequently inserted in particular into the receptacle of a protective cap.

According to a first variant of the invention, a first layer of a first sheet-like material and a second layer of a second sheet-like material are continuously fed in the form of sheet-like bands. If the intention is for more layers to be used, further sheet-like bands are to be provided accordingly.

In an overlapping region of the bands, the at least two layers are pressed together by a top-side stamp and a bottom-side stamp and a cut is made in a manner surrounding the stamps using a cutting contour, by way of which cut the two layers of the sheet-like structure provided for the protective cap or for the venting insert are separated from the sheet-like bands. At this point in time, the two layers, which are not connected fixedly to one another, are held between the two stamps.

This multi-layer sheet-like structure is subsequently inserted into an injection moulding cavity in a state fixed by the stamps. A plastic material, for example HDPE or PP, is then injected into the injection moulding cavity, which plastic material forms a common bearing structure, which, on one side or integrally on both sides of the sheet-like structure, projects over the boundary region of the sheet-like structure and fixes the layers of the sheet-like structure.

The stamps on both sides are spaced apart from the sheet-like structure after the bearing structure has cured and, in this case, open up the paths from the external surroundings to the sheet-like structure and from the sheet-like structure into an inner region of the protective cap.

The special feature in the method described is, in particular, that the same means, specifically the two stated stamps, are used to press together the at least two layers, which are not connected to one another at this point in time, and to position them in the cavity such that, during injection moulding, they are held at the desired location and, there, are surrounded by plastic. Here, the stamps themselves keep the venting aperture free of plastic on both sides of the sheet-like structure.

In an alternative method, it is provided that, firstly, a main body of a vented protective cap or of a venting insert, which has a venting aperture which is surrounded by a bearing structure having a ring-shaped fastening surface, is provided.

A first layer of the sheet-like structure and a second layer of the sheet-like structure are placed in succession or together in the venting aperture such that the boundary region of the first layer comes into contact with the ring-shaped fastening surface and the boundary region of the second layer comes into contact with the boundary region of the first layer.

For the purpose of fastening the layers to one another or to the ring-shaped fastening surface, thermal joining-together of the boundary regions of the first layer and second layer is effected by means of a heated stamp after insertion of the second layer.

The use of the heated stamp may be realized once after the introduction of the second layer. In this case, it is then also the case that the first layer is fastened, indirectly, to the ring-shaped fastening region. Alternatively, it is however also possible for the heated stamp to be used multiple times, in particular once per layer. The boundary region of the first layer is thus, by means of the heated stamp, already thermally bonded to the ring-shaped fastening surface after the placement of the first layer and before the placement of the second layer.

BRIEF DESCRIPTION OF THE DRAWINGS

Further advantages and aspects of the invention will emerge from the claims and from the following description of preferred exemplary embodiments of the invention, which are explained below on the basis of the figures.

FIGS. 3A to 3C show three variants of vented protective caps in a sectional illustration.

FIGS. 6 and 7A to 7H illustrate a first method for producing a protective cap according to the invention.

DETAILED DESCRIPTION OF THE EXEMPLARY EMBODIMENTS

Figure 1:
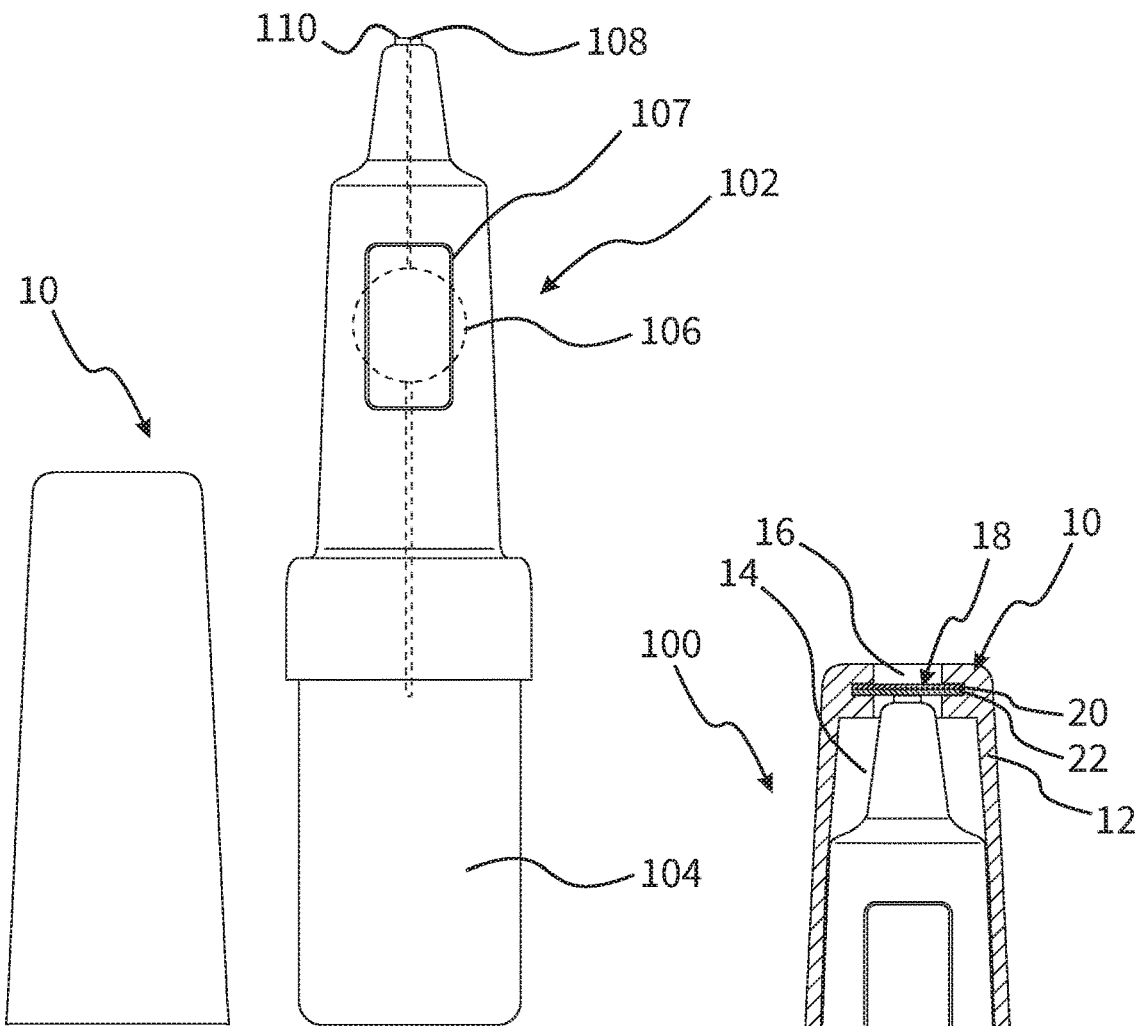
FIGS. 1 and 2 show a dispenser according to the invention with a vented protective cap which has a venting aperture which is covered by means of a flexible sheet-like structure.
Figure 2:
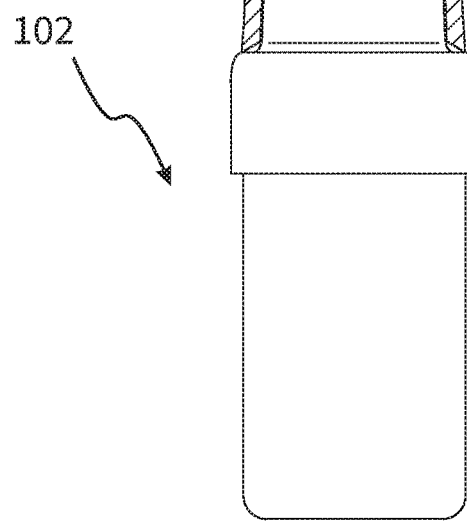

FIGS. 1 and 2 show a liquid dispenser 100 according to the invention.

Said liquid dispenser comprises a main unit 102 in which a liquid store 104, a conveying device 106 and a discharge opening 108 are provided. The conveying device 106 is provided for guiding liquid from the liquid store 104 to the discharge opening 108. In this case, various technical designs are conceivable, in particular those of a design of the dispenser having a pressure store 104 and a conveying device 106 which is designed as a switching valve. As soon as a user pushes an actuating button 107, the switching valve is opened and the liquid pressurized in the liquid store 104 flows to the discharge opening 108. As an alternative thereto, the conveying device 106 may be designed as a pump device 106. At any rate, the liquid is stored free of pressure in the liquid store 104 and is pumped to the discharge opening 108 by actuating the pump device 106 by means of the actuating button 107. Other designs, for example having a squeeze bottle which is simultaneously a liquid store and a conveying device, are also possible.

The liquid dispenser in FIGS. 1 and 2 is a drop dispenser and, as such, has, in a manner surrounding the discharge opening 108, a drop formation geometry 110, for example a planar or concave ring-shaped surface, to which a drop, in an upside-down position of the dispenser, can adhere until it is detached from the drop formation geometry 110 under the action of gravitational force.

The liquid dispenser 100 has a protective cap 10, which is formed as a vented protective cap. This means that a cap interior 14 is connected to a surrounding atmosphere via a venting aperture 16. In the case of the configuration of this exemplary embodiment, the venting aperture 16 is provided on an end surface of a cap wall 12 of the protective cap 10. The venting aperture 16 is provided with a sheet-like structure 18, this being a flexible sheet-like structure which is made up of multiple flexible layers having different properties, as will be explained in more detail below. The exemplary sheet-like structure 18 illustrated in FIG. 2 has two layers, of which an inner layer 22 is formed as an absorbent pad and, after the protective cap 10 is mounted onto the main unit 102, is able to absorb a residual drop remaining in the region of the drop formation geometry 110 and, if appropriate, to kill germs contained therein by way of an antibacterial configuration. That side of the sheet-like structure 18 which faces away from the discharge opening 108 is formed by an outer layer 20, which may be formed for example as a sterile filter, so that, with the protective cap 10 mounted, an introduction of germs into the cap interior 14 is avoided.

FIGS. 3A to 3C show three variants of the protective cap 10, of which the variants in FIGS. 3A and 3C are also explained in more detail below with regard to their respective production.

In the design as per FIG. 3A, the protective cap 10 has a main body 8, which main body 8 forms both the lateral surfaces or lateral wall of the protective cap 10, and a mounting element, which mounting element forms a bearing structure 24 provided in a manner surrounding the venting aperture 16 and extending on both sides of the sheet-like structure 18 over the latter and thereby securing the two layers 20, 22. The layers 20, 22 are not connected fixedly to one another. To illustrate this, a small gap between the layers 20, 22 is shown in FIG. 3A. In practice, however, the layers 20, 22 will bear against one another at least in their boundary regions 20A, 22A, but in particular will bear against each other completely. Said layers, however, at least in a central region, are not connected directly to one another and, as will be explained in more detail below, are normally not connected to one another prior to attachment to the main body of the protective cap. The layers 20, 22 are, by the bearing structure 24, secured to one another only in the fitted state, as is illustrated for example in FIG. 3A.

In the variant as per FIG. 3B, the mounting element which forms the bearing structure 24 is formed differently, since only on one side, below the sheet-like structure 18 in the present case, does it extend over the boundary region 18A thereof. However, the bearing structure 24 does not project upwardly beyond the layers 20, 22. Instead, the layers 20, 22, and in particular the outer layer 20, are fastened to the main body 8 of the protective cap in that said main body is, in the manner explained in more detail below, injection-moulded onto the layer 20, which is placed in a cavity beforehand, wherein a boundary region 20A of the layer 20 is connected in a materially bonded manner to the main body 8.

In the design as per FIG. 3C, it is again the case that provision is not made of a mounting element or bearing structure provided on both sides of the sheet-like structure 18. Instead, a bearing structure 26 having a fastening surface 28 only above the sheet-like structure 18 is provided. As is illustrated by the relatively thin boundary regions in FIG. 3C, the layers 20, 22 of the sheet-like structure 18 have in this case been thermally bonded to the stated fastening surface 28 together or in succession by means of an embossing stamp.

A special feature with the design in FIG. 3C is a protective structure 29 which is formed as a separate component and which, on the outer side, is pushed into the venting aperture 16 and, there, is held in a force-fitting manner. Said protective structure protects the sheet-like structure and prevents in particular damage to a layer acting as a sterile filter. The protective structure 29 is illustrated in the design in FIG. 3C merely by way of example and could also likewise be provided in the other cap designs described here.

With regard to the designs in FIGS. 3A and 3C, FIGS. 4A to 4D show two different constructions in each case. The designs in FIGS. 4A and 4C correspond here to those in FIGS. 3A and 3C.

Figure 4A:
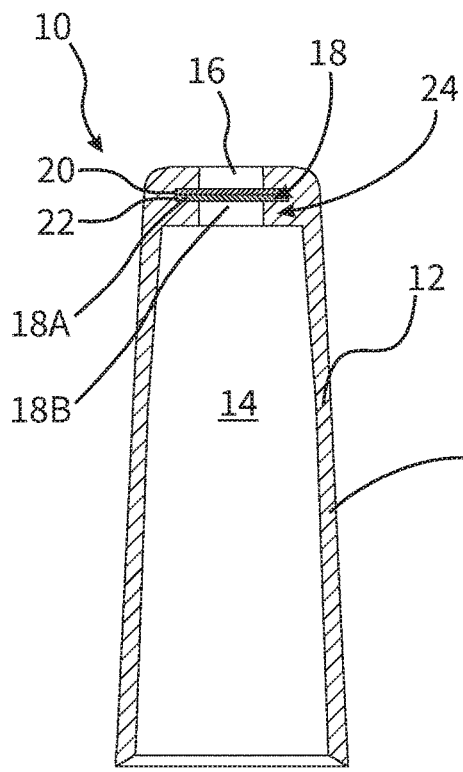
FIGS. 4A to 4D illustrate, in addition to the designs in FIGS. 3A and 3C, the possibility of direct connection of the main body of the protective cap to the flexible sheet-like structure and also of the use of a separate venting insert.
Figure 4B:
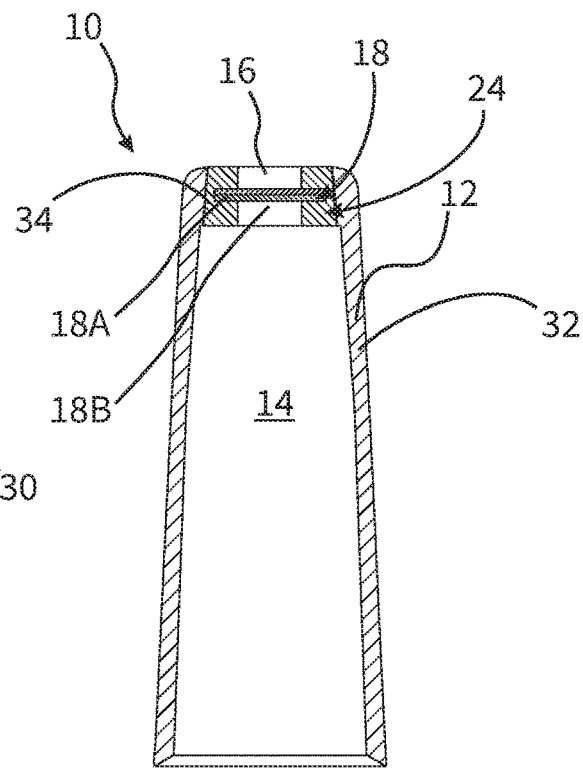
Figure 4C:
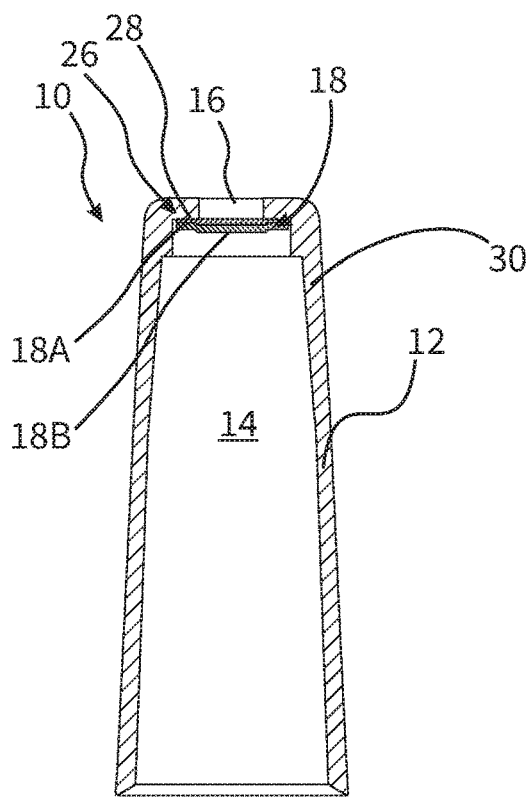

By contrast, a design in which a mounting element in the form of a venting insert 34 is attached at an end side of a main component 32 of the protective cap 10, said main component 32 forming in particular also the lateral wall 12 and having the venting aperture 16 formed in the venting insert 34 and the sheet-like structure 18 located in the venting insert 34, is shown by the variant in FIG. 4B. The venting insert 34 is fastened in the main component 32 of the protective cap 10 by means of a press fit. Alternative fastenings, such as adhesive connections, welded connections and threaded connections, are also possible here.

Figure 4D:
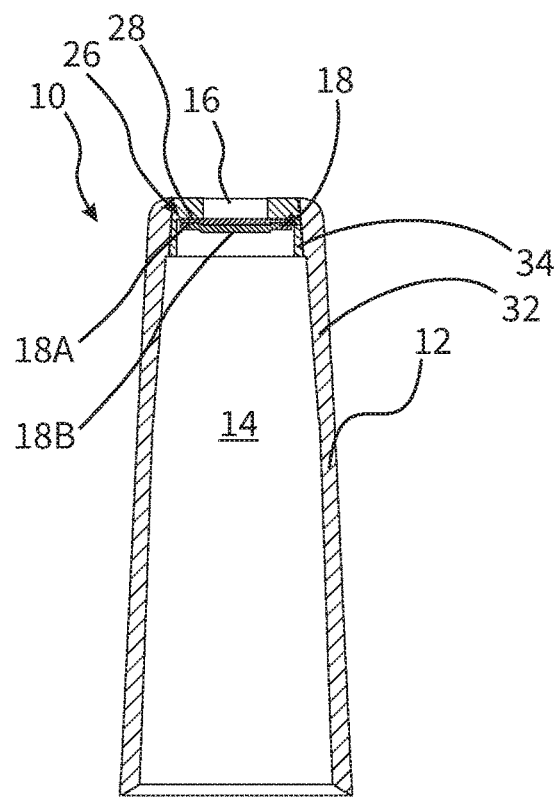

Corresponding to the variant in FIG. 4B, provision is also made in the variant in FIG. 4D of a separate venting insert 34, which provides the bearing structure 26 with the fastening surface 28 and which, in the same manner as the venting insert 34 in FIG. 4B, is inserted into the main component 32 of the protective cap 10 by means of a press fit.

FIGS. 5A to 5D illustrate different configurations of single layers, which together form the sheet-like structure 18. Since it is provided according to the invention that the layers of the sheet-like structure are not connected to one another, or at least not in a central region, it is advantageously possible in a simple manner for provision to be made of particular combinations of layers for particular usage cases. A technically cumbersome production of a composite band, from which the sheet-like structure is extracted, that is cost-effective only for large quantities is therefore not necessary. The configurations shown here by way of example each have a sterile filter. The separation limit of said sterile filter is in size preferably at most 1 µm, preferably at most 0.5 µm. An even finer separation limit of at most 0.5 µm in size may also be advantageous.

Figure 5A:
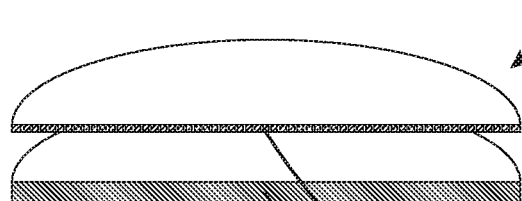
FIGS. 5A to 5D show different configurations of layers of the flexible sheet-like structure.

FIG. 5A shows a design in which a sterile filter 21A and an absorbent layer 21C together form the sheet-like structure 18. Here, the sterile filter 21A is shown fairly thin in order to illustrate that, in this case, it is a membrane filter, that is to say a filter which comprises a multiplicity of pores, each of which is smaller than a predefined separation limit so as not to allow particular constituents, such as bacteria, to pass through.

Figure 5B:
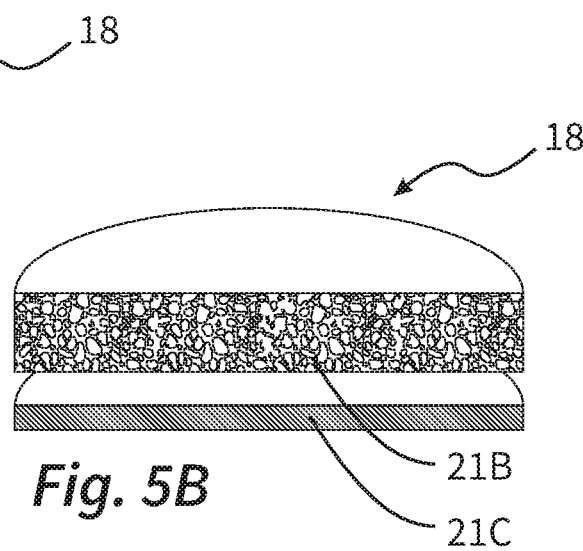

In the variant as per FIG. 5B, provision is likewise made of a sterile filter 21B. This is formed as a deep-bed filter, however. This means that, although not every single pore of the filter is smaller than the intended separation limit, the filter, on account of its thickness, is still able to reliably filter out constituents which are larger than the separation limit.

Whereas for the membrane filter 21A in FIG. 5A the constituents separated out by the filter remain on the top side of the filter, for the deep-bed filter 21B in FIG. 5B, said constituents pass into the filter itself and, there, are separated from the air passing through.

Figure 5C:
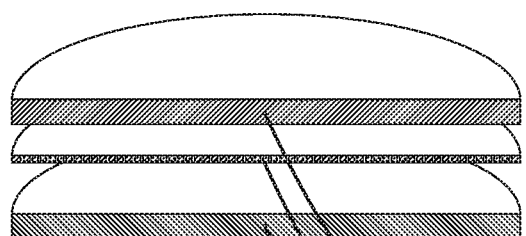

The design in FIG. 5C provides that, in addition to a sterile filter 21A and an absorbent pad 21C, provision is made of a screening layer 21E. This primarily performs the function of screening the sterile filter 21A from view. Since the sterile filter 21A furthermore normally has a different colouring from the protective cap 10, it has been found that users erroneously assume that the sterile filter 21A is to be removed upon initial operation of the dispenser. By way of the stated screening layer 21E, which is furthermore designed with the same colouring as the protective cap 10, the presence of a clearly differently coloured sterile filter 21A is screened from view, and so the user does not arrive at the idea of damaging the sheet-like structure 18.

Figure 5D:
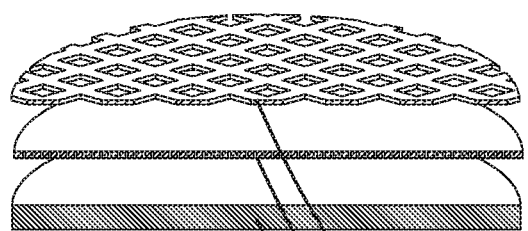

In the design as per FIG. 5D, a sterile filter layer 21A and an absorbent layer 21C for absorbing a residual drop are again provided. Here, however, provision is furthermore made of a support layer 21D, which is comparatively firm and thus protects the sterile filter 21A mechanically against inadvertent or deliberate damage.

Figure 6:
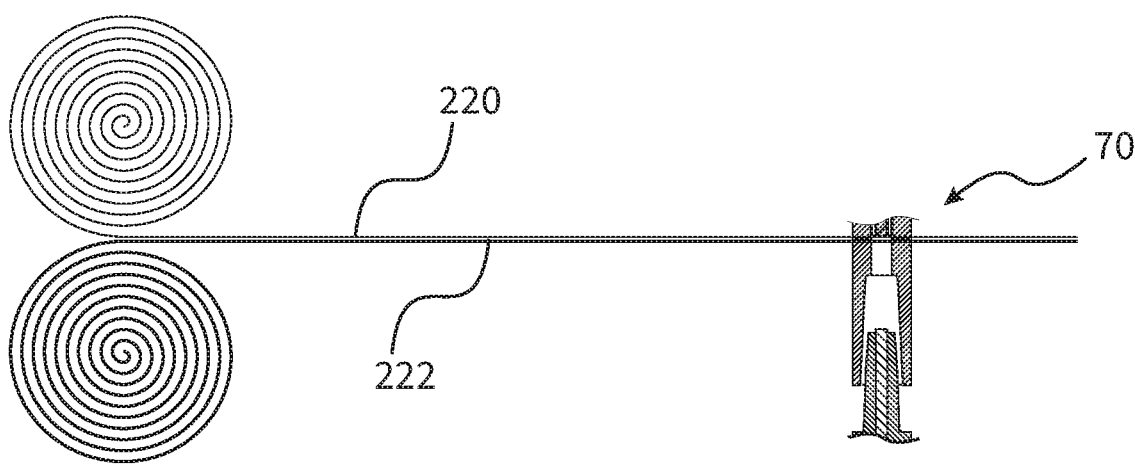

FIGS. 6 to 7H show a first method for producing a protective cap of the described type, this being in the present case that protective cap which is also illustrated in FIGS. 3A and 4A.

FIG. 6 schematically shows the basic construction. Two bands 220, 222 are fed to a combined punching and injection moulding tool 70. FIGS. 7A to 7H show the processing of said bands 220, 222 and the production of the protective cap 10 in the region of said punching and injection moulding tool 70.

FIG. 7A shows an initial state. In said state, a cavity 90, which is primarily delimited by a top shell 72 and a bottom shell 74, is still open. The above-described bands 220, 222 are moved into two slots of the top shell 72. The bottom shell 74 is provided centrally with a vertically displaceable stamp 82 in an aperture of the bottom shell 74. Correspondingly, the top shell 72 is provided with a likewise vertically displaceable stamp 80 and with a cutting contour 84 which is movable independently thereof and which surrounds the stamp 80. The stamp 80 and the cutting contour 84 are arranged in an aperture of the top shell 72.

In the initial state in FIG. 7A, the stamp 80 and the cutting contour 84 are situated above the slots through which the bands 220, 222 are fed.

Taking this as a starting point, firstly the stamp 82 is displaced vertically from the bottom upwards until it bears against the bottom side of the lower band 222. The top stamp 80 and the cutting contour 84 simultaneously push from above onto the band 220 such that the bands 220, 222 are pressed together. The state in FIG. 7B is established.

In the manner illustrated by FIG. 7C, the stamps 80, 82 and the cutting contour 84 then together move vertically downwards, whereby the sheet-like structure 18 consisting of two layers 20, 22 is separated from the surrounding bands 220, 222 in that the cutting contour 84 shears it off at the boundary of the aperture in the top shell 72. The stamps 80, 82 and the cutting contour 84 move together to the position which is illustrated in FIG. 7D.

Proceeding from here, the stamps 80, 82 move a little further, while at the same time or separately therefrom the bottom shell 74 and the top shell 72 are moved to one another, so that the cavity 90 is closed. With the lowering of the stamps 80, 82 into the position in FIG. 7E, the cutting contour 84 is no longer moved along therewith, and so a relative displacement between the cutting contour 84 and the stamp 80 occurs for the first time. The cutting contour 84 remains further above and thus forms with its end side facing downwards a part of the delimiting wall of the cavity 90.

Although the stated step, in which the stamps 80, 82 are displaced relatively with respect to the cutting contour, is considered to be advantageous, it is not essential. The above-described design in FIG. 3B can be produced by means of a method which is largely the same as the method described here, albeit with the stated relative displacement not being provided. For such a method, provision may be made of a tool with which the cutting contour 84 and the stamp 80 are formed as a common component.

Proceeding from the state in FIG. 7E, liquid plastic, for example PP or HDPE, is then guided through a feed opening (not illustrated) into the cavity 90, as can be seen in FIG. 7F. The plastic 92 cures in the cavity 90, with the result that, subsequently, in the manner illustrated by FIGS. 7G and 7H, after the bottom shell 74 and the top shell 72 are spaced apart, the finished protective cap 10 can be removed.

An alternative method is illustrated in FIGS. 8A to 8D. Said method proceeds from a main body 8 of the protective cap 10 that has already been fully produced by injection moulding and in which a venting aperture 16 is provided at an end side. The latter breaks through a bearing structure 26 which is formed primarily by a fastening surface 28.

Figure 8A:
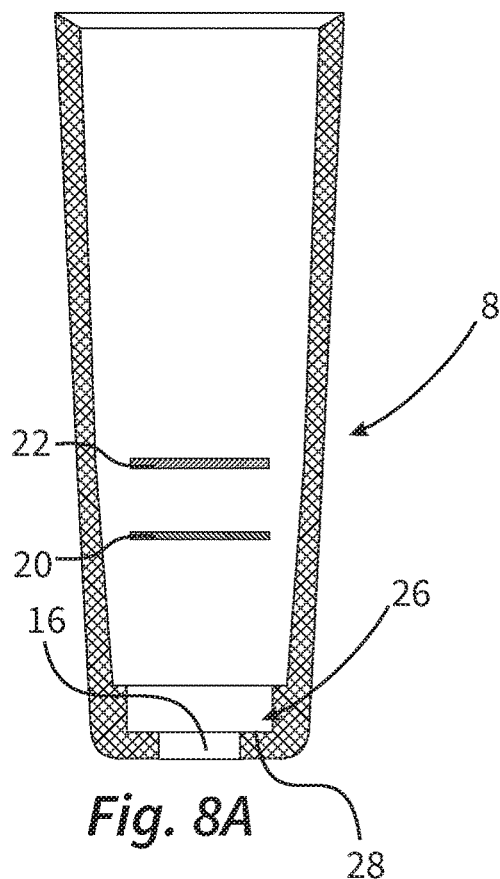
FIGS. 8A to 8D and 9A to 9F illustrate two variations of an alternative method for producing a protective cap according to the invention.
Figure 8B:
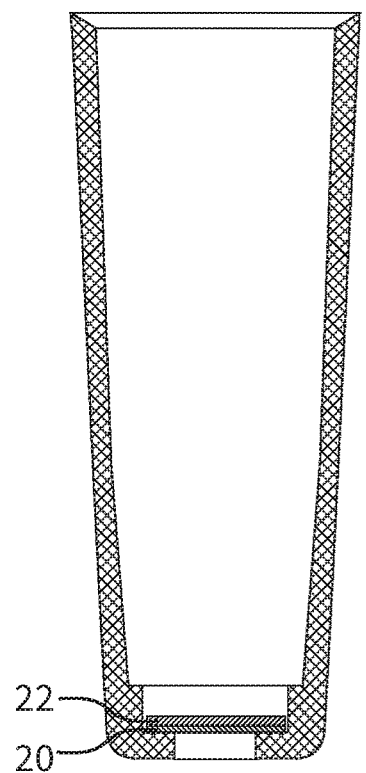

The two layers 20, 22 of the sheet-like structure 18 are individually inserted into said main body 8. Said layers are not connected fixedly to one another at this point in time, but may of course, in deviation from FIG. 8A, be introduced in a form in which they already bear on one another. The two layers 20, 22 have a surface which is larger than the cross-sectional surface of the venting aperture 16, with the result that they come to bear on the fastening surface 28, as FIG. 8B shows.

Figure 8C:
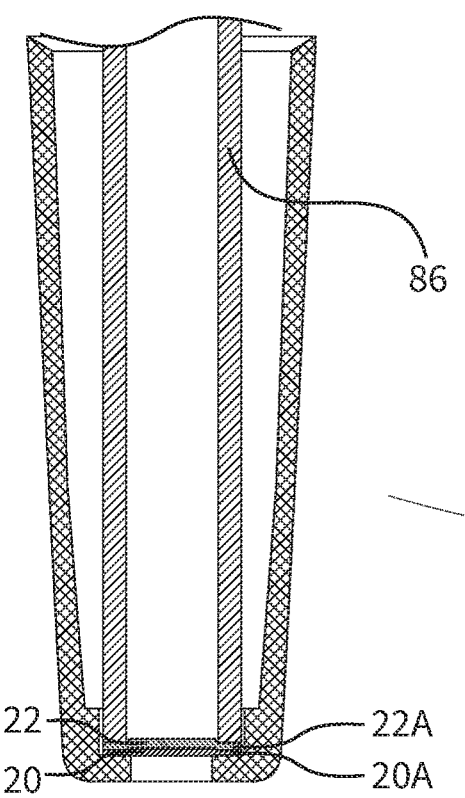
Figure 8D:
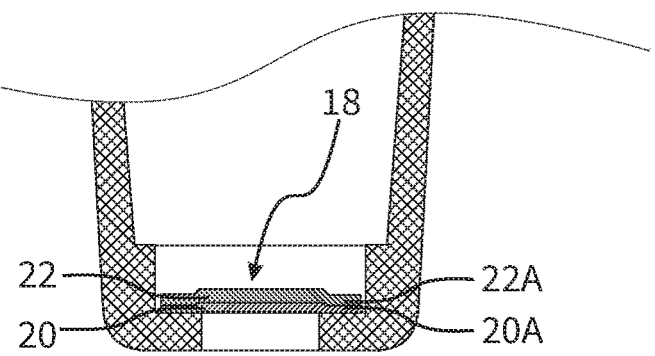

Subsequently, a heated embossing stamp 86 is introduced into the main body 8 from above in the manner illustrated by FIG. 8C. The ring-shaped end surface of the embossing stamp is used for pressing the boundary regions 20A, 22A of the layers 20, 22 against the fastening surface 28 and in the process thermally bonding them together and to the fastening surface 28. The result is the two-layer structure which can be seen in FIG. 8D.

Figure 9A:
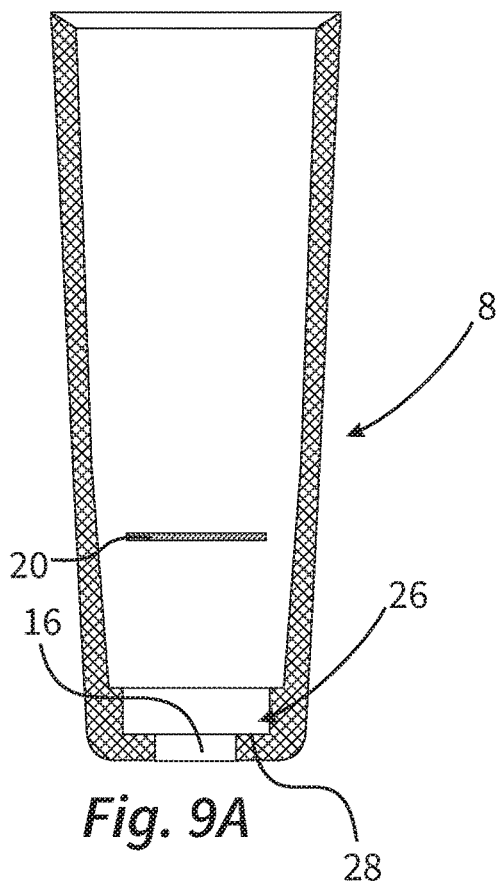
Figure 9B:
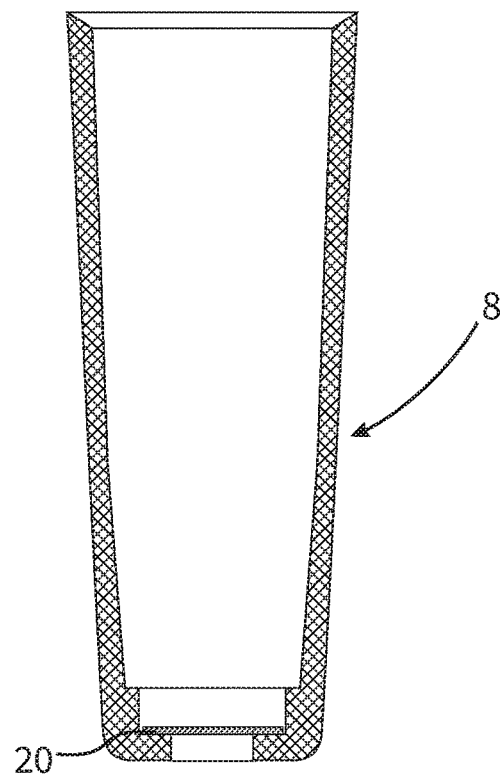
Figure 9C:
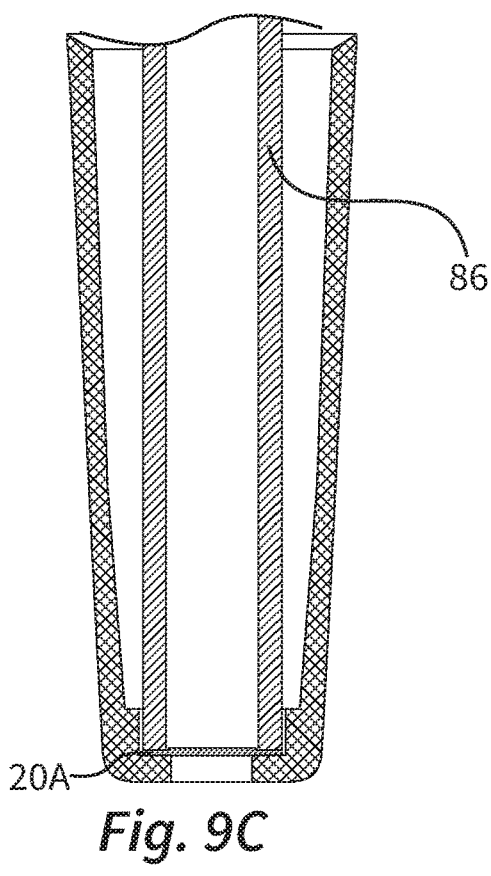
Figure 9D:
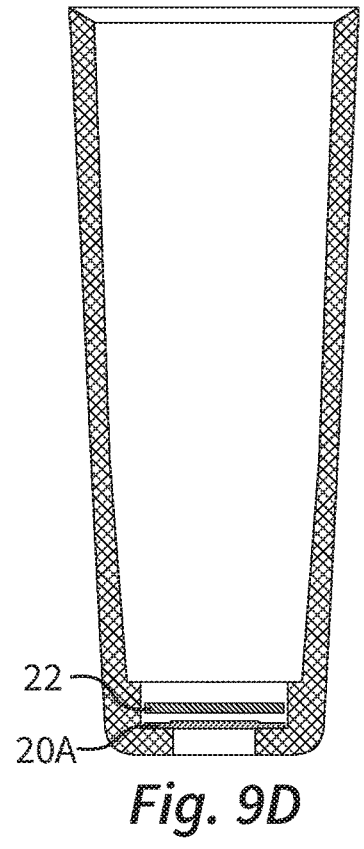
Figure 9E:
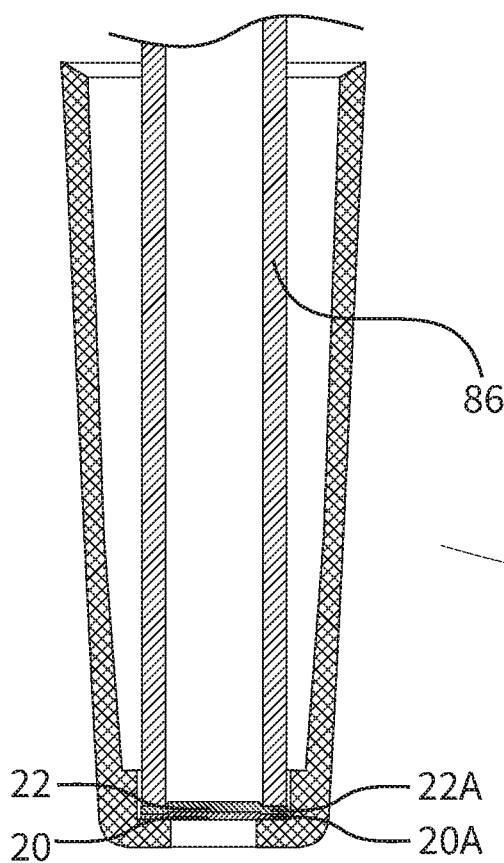

An alternative method to this emerges from FIGS. 9A to 9F. Here, the two layers 20, 22 are inserted in succession. As shown in FIGS. 9A to 9C, firstly a first layer 20 is placed on the fastening surface 28 and thermally fastened there by means of the embossing stamp 86. The second layer 22 is introduced only afterwards, this then, in the manner illustrated by FIG. 9E, being likewise fastened by means of the heated embossing stamp 86, specifically on the layer 20 already fastened beforehand.

Figure 9F:
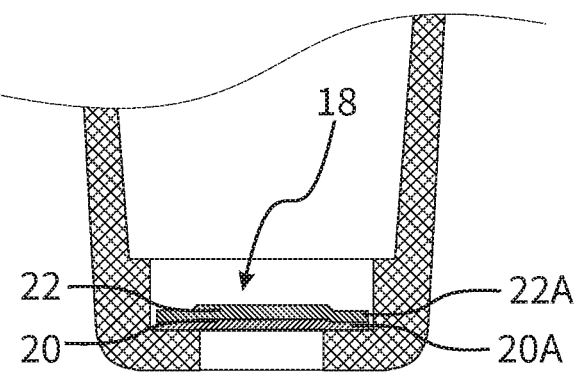

As FIG. 9F shows, this results in a construction similar to that in the method in FIGS. 8A to 8D. Even though the method in FIGS. 9A to 9F comprises more manufacturing steps, it is hereby possible for better tightness to be obtained in the boundary region according to material of the layers 20, 22, and so this more complex method has its advantages.

The invention claimed is:

1. A liquid dispenser comprising:
  a main unit having a liquid store, a conveying device and a discharge opening for releasing the liquid; and
  a protective cap able to be mounted onto the main unit and protecting the discharge opening in a mounted state, the protective cap having a cap wall surrounding a cap interior, the cap wall having a venting aperture spanned by a flexible sheet structure, a boundary region of the sheet structure being fixed in an encircling manner to a boundary of the venting aperture, the sheet structure comprising at least two layers bearing directly against one another but, at least in a central region of the sheet structure, not being connected fixedly to one another.

2. The liquid dispenser according to claim 1, wherein the at least two layers of the sheet structure are held at the boundary of the venting aperture by an injection-molded bearing structure, and the bearing structure, on one side or on both sides of the sheet structure, projects over the boundary region of the sheet structure.

3. The liquid dispenser according to claim 1, further including a bearing structure having a ring-shaped fastening surface provided at the boundary of the venting aperture, a first one of the two layers of the sheet structure is, in a boundary region of the first layer, thermally fastened to the fastening surface and a second one of the two layers of the sheet structure is, in a boundary region of the second layer, thermally fastened to the boundary region of the first layer.

4. The liquid dispenser according to claim 1, wherein the protective cap has a main component comprising the cap wall, the cap wall forming a lateral wall of the protective cap, the main component further comprising a bearing structure integral with the lateral wall and configured to support the sheet structure, and the bearing structure defines the venting aperture.

5. The liquid dispenser according to claim 1, wherein the protective cap has a main component comprising the cap wall and—an opening disposed adjacent the discharge opening, the cap wall forming a lateral wall of the protective cap and the protective cap has a venting insert inserted sealingly into the opening and comprising a bearing structure configured to hold and surround the sheet structure.

6. The liquid dispenser according to claim 1, wherein:
  at least one of the two layers of the sheet structure is formed by a sterile filter having a separation limit of at most 1 μm in size; and/or
  at least one of the two layers of the sheet structure is an absorbent layer provided for absorbing a residual drop from the discharge opening of the dispenser, wherein, proceeding from the cap interior, said at least one layer comprises the first layer of the sheet structure; and/or
  at least one of the two layers of the sheet structure is formed as a deep-bed filter; and/or
  at least one of the two layers of the sheet structure is formed as a membrane filter; and/or
  at least one of the two layers of the sheet structure has a hydrophilic surface; and/or
  at least one of the two layers of the sheet structure is formed as an antibacterial layer and comprises a bactericidal constituent; and/or
  at least one of the two layers of the sheet structure is formed as a support layer; and/or
  at least one of the two layers of the sheet structure is an outermost layer and is formed as a screening layer and has a color uniform with respect to a surrounding bearing structure; and/or
  the protective cap has a protective structure for protecting the sheet structure, wherein the protective structure is formed as a component separate from a bearing structure and connected in a force-fitting manner or form-fitting manner to the bearing structure.

7. The liquid dispenser according to claim 5, wherein:
  the venting insert has a tapering lateral surface for simplified fitting into the opening of the protective cap; or
  the venting insert is fastened in the opening of the protective cap by a snap-action connection; or
  the venting insert is fastened in the opening of the protective cap by a threaded connection; or
  the venting insert is fastened in the opening of the protective cap by an adhesive or welded connection.

8. The liquid dispenser according to claim 1, wherein at least one of the two layers of the sheet structure comprises an absorbent or antibacterial layer, said at least one layer, with the protective cap mounted on the main unit, is arranged directly above the discharge opening such that a residual drop remaining at the discharge opening can be absorbed and/or decontaminated by said at least one layer.

9. The liquid dispenser according to claim 1, wherein:
  the liquid dispenser is designed as a drop dispenser and has, in a manner surrounding the discharge opening, a drop formation geometry; and/or the liquid dispenser is filled with a pharmaceutical liquid; and/or the conveying device of the liquid dispenser comprises a pump device for conveying the liquid from the liquid store to the discharge opening; and/or the conveying device of the liquid dispenser comprises a squeeze bottle able to be compressed for the purpose of conveying the liquid from the liquid store to the discharge opening; and/or the liquid dispenser has a pressure store; and/or the liquid dispenser is designed as a spray dispenser to release the liquid in atomized form.

10. The liquid dispenser according to claim 5, wherein the venting insert defines the venting aperture in the cap wall.

11. A liquid dispenser comprising:

a main unit comprising a liquid store, a discharge opening and a conveying device configured to convey liquid from said liquid store to said discharge opening; and a protective cap having a cap wall disposed in surrounding relation with an interior of said protective cap, said protective cap being mounted on said main unit in a mounted state and in the mounted state being disposed to protect said discharge opening, said protective cap having a mounting element on said cap wall adjacent said discharge opening, said mounting element including a venting aperture disposed adjacent said discharge opening in the mounted state of said protective cap, said protective cap further comprising a flexible sheet arrangement spanning said venting aperture and disposed between said discharge opening and the external environment of said liquid dispenser to close off said venting aperture from the external environment, said flexible sheet arrangement including an outer periphery fixed to said mounting element along a periphery of said venting aperture, said flexible sheet arrangement comprising at least first and second sheet layers, said first and second sheet layers being in direct contact with one another but not being fixedly connected to one another at least in a central region of said flexible sheet arrangement.

12. The liquid dispenser according to claim 11, wherein said cap wall comprises a lateral wall portion disposed adjacent said conveying device of said main unit and an end wall portion connected to said lateral wall portion and disposed adjacent said discharge opening, said mounting element being integral with said end wall portion and together therewith forming a bearing structure, said bearing structure being disposed to overlap said outer periphery of said flexible sheet arrangement to secure said flexible sheet arrangement at said periphery of said venting aperture.

13. The liquid dispenser according to claim 12, wherein said flexible sheet arrangement has a first side disposed to face said discharge opening and a second side disposed to face away from said discharge opening, and said bearing structure overlaps said outer periphery of said flexible sheet arrangement on both said first and second sides or on one of said first side or said second side.

14. The liquid dispenser according to claim 11, wherein said cap wall comprises a lateral wall portion disposed adjacent said conveying device of said main unit, said lateral wall portion having an opening and said mounting element comprising an insert sealingly disposed in said opening and forming a bearing structure disposed to overlap said outer periphery of said flexible sheet arrangement to secure said flexible sheet arrangement at said periphery of said venting aperture.

15. The liquid dispenser according to claim 14, wherein said flexible sheet arrangement has a first side disposed to face said discharge opening and a second side disposed to face away from said discharge opening, and said bearing structure overlaps said outer periphery of said flexible sheet arrangement on both said first and second sides or on one of said first side or said second side.

16. The liquid dispenser according to claim 11, wherein said flexible sheet arrangement has a first side disposed to face said discharge opening and a second side disposed to face away from said discharge opening, said first sheet layer being disposed at said first side of said flexible sheet arrangement immediately adjacent said discharge opening such that a residual drop of liquid remaining at said discharge opening is absorbed by said first sheet layer.

17. The liquid dispenser according to claim 16, wherein said second sheet layer comprises a sterile filter and is disposed at said second side of said flexible sheet arrangement to prevent introduction of contaminants into said cap interior.

18. The liquid dispenser according to claim 11, wherein said first and second sheet layers are positionally fixed relative to one another only when said flexible sheet arrangement is mounted to said protective cap.

* * * * *